US012349672B2

(12) United States Patent
Rubinsky et al.

(10) Patent No.: US 12,349,672 B2
(45) Date of Patent: Jul. 8, 2025

(54) PROCESS AND DEVICE FOR TEMPERATURE AND PRESSURE CONTROLLED CRYOPRESERVATION

(71) Applicant: The Regents of the University of California, Oakland, CA (US)

(72) Inventors: Boris Rubinsky, El Cerrito, CA (US); Gabriel Nastase, El Cerrito, CA (US); Gideon Ukpai, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 566 days.

(21) Appl. No.: 16/637,735

(22) PCT Filed: Aug. 9, 2018

(86) PCT No.: PCT/US2018/046099
§ 371 (c)(1),
(2) Date: Feb. 7, 2020

(87) PCT Pub. No.: WO2019/032889
PCT Pub. Date: Feb. 14, 2019

(65) Prior Publication Data
US 2020/0178518 A1  Jun. 11, 2020

Related U.S. Application Data

(60) Provisional application No. 62/544,219, filed on Aug. 11, 2017.

(51) Int. Cl.
*A01N 1/162* (2025.01)
*A01N 1/125* (2025.01)
(Continued)

(52) U.S. Cl.
CPC .............. *A01N 1/162* (2025.01); *A01N 1/145* (2025.01); *G01N 7/00* (2013.01); *A01N 1/125* (2025.01);
(Continued)

(58) Field of Classification Search
CPC ........ A01N 1/165; A01N 1/147; A01N 1/125; A01N 1/145; A01N 1/162; A01N 1/0284; A01N 1/0257; A01N 1/0221; A01N 1/0268; A01N 1/0289; B01L 2300/1894; G01N 7/00
(Continued)

(56) References Cited

U.S. PATENT DOCUMENTS 4,199,022 A    4/1980  Senkan et al.
6,209,387 B1*  4/2001  Savidge ............... G01N 29/326
                                          73/24.05
(Continued)

OTHER PUBLICATIONS

Muldrew et al., "Transplatnation of articular cartilage following a step-cooling cryopreservation protocol," Cryobiology, 43(3):260-267, 2001.
Muldrew et al., "Evidence of chondrocyte repopulation in adult ovine articular cartilage following cryoinjury and long-term transplantation," Osteoarthritis Cartilage, 9(5):432-439, 2001.
(Continued)

*Primary Examiner* — Michael L Hobbs
*Assistant Examiner* — Lenora A Abel
(74) *Attorney, Agent, or Firm* — Rudy J. Ng; Dana Lim; Bozicevic, Field & Francis LLP (57) ABSTRACT

The disclosure provides processes for temperature and pressure controlled cryopreservation of samples by using isochoric systems.

13 Claims, 8 Drawing Sheets

(51) Int. Cl.
  *A01N 1/145*  (2025.01)
  *A01N 1/147*  (2025.01)
  *A01N 1/165*  (2025.01)
  *G01N 7/00*  (2006.01)

(52) U.S. Cl.
  CPC .............. *A01N 1/147* (2025.01); *A01N 1/165* (2025.01); *B01L 2300/1894* (2013.01)

(58) Field of Classification Search
  USPC ......................................................... 435/1.3
  See application file for complete search history.

(56) References Cited

U.S. PATENT DOCUMENTS

| | | |
|---|---|---|
| 2006/0063141 A1 | 3/2006 | McGann et al. |
| 2007/0042337 A1* | 2/2007 | Rubinsky ............... A01N 1/125 422/1 |
| 2009/0011505 A1 | 1/2009 | Leunissen |
| 2016/0299047 A1* | 10/2016 | Molla ............... B01L 3/502784 |

OTHER PUBLICATIONS

Wikipedia, "Cryopreservation" Version: Jul. 18, 2017, https://en.wikipedia.org/w/index.php?title=Cryopreservation&oldid=791134471.

Young, Lee W., International Search Report and Written Opinion, United States Patent and Trademark Office, PCT/US2018/046099, Jan. 22, 2019.

Lee, Sun Hwa, International Preliminary Report on Patentability and Written Opinion, The International Bureau of WIPO, PCT/US2018/046099, Feb. 20, 2020.

Kuster, Gunilla, Extended European Search Report, Application No. 18843257.9, European Patent Office, Feb. 25, 2021.

Nastase, Gabriel et al., "Isochoric and isobaric freezing of fish muscle", Biochemical and Biophysical Research Communications, vol. 485, No. 2, Feb. 20, 2017, pp. 279-283.

Rubinsky, B et al., "The thermodynamic principles of isochoric cryopreservation", Cryobiology, vol. 50, No. 2, Apr. 1, 2005, pp. 121-138.

Ukpai, Gideon et al., "Pressure in isochoric systems containing aqueous solutions at subzero Centigrade temperatures", PLOS One, vol. 12, No. 8, Aug. 17, 2017, pp. 1-16.

* cited by examiner

PROCESS AND DEVICE FOR TEMPERATURE AND PRESSURE CONTROLLED CRYOPRESERVATION

CROSS REFERENCE TO RELATED APPLICATIONS

This application claims priority to International Application No. PCT/US2018/046099, filed Aug. 9, 2018, which application claims priority under 35 U.S.C. § 119 from Provisional Application Ser. No. 62/544,219 filed Aug. 11, 2017, the disclosures of which are incorporated herein by reference.

TECHNICAL FIELD

The disclosure provides processes for temperature and pressure controlled cryopreservation of samples by using isochoric systems.

BACKGROUND

Long term preservation of biological materials at subfreezing temperature, cryopreservation, has become essential to many applications in medicine; from clinical applications—such as preservation of frozen oocytes to Nobel prize enabling research—such as cryopreservation of *C. elegans*.

SUMMARY

There is growing interest in developing cryopreservation technology for long term preservation of biological organs at cryogenic temperatures. Until now temperature measurements were considered the most important thermodynamic variable in the design and control of cryopreservation protocols. In a one phase system, two thermodynamic properties are needed to define the system. In cryopreservation, it is usually assumed that the pressure is isobaric (constant) and the volume is constant. However, this assumption is not verified, and in cryopreservation protocols, pressure and volume are not monitored. Pressures and volumes may change depending on the configuration of the vessel and the vessel material used.

Provided herein are results of studies that indicate a more reliable means for designing and controlling cryopreservation protocols by measuring and monitoring both temperature and pressure of the system. In particular, using an isochoric (constant volume) system, instrumented with means to monitor pressure and temperature, the freezing and thawing of pure water to $-180°$ C. was examined. Results show that measuring temperature and pressure during freezing and thawing provides precise insight into the thermodynamic state of the ice. For example, the pressure at $-30°$ C. was unexpectedly found to be substantially higher than at the triple point and that the ice that forms from $-40°$ C. to $-180°$ C., is ice I, not ice II or III.

Cryopreservation by vitrification (glass formation) is an area of great interest for cryopreservation. Measuring pressures and temperatures of pure water with different concentrations of dimethyl sulfoxide (DMSO) (a chemical compound of interest in cryopreservation), it was found that the pressure measurement can provide a simple means to gain information on the occurrence of vitrification and devitrification during the cryopreservation process. The data presented herein provides clear evidence that adding pressure measurements to temperature measurements are an important tool in the design, optimization and control of cryopreservation protocols and methods.

The disclosure provides methods and systems for freezing samples. The disclosure provides a process for the cryopreservation of a sample, comprising placing a biological sample in an isochoric system; reducing the temperature of the isochoric system until a subfreezing temperature is reached for the biological sample, wherein the temperature is reduced in controlled manner comprising: (i) cooling the biological sample until a first temperature is reached; (ii) maintaining the sample at the first temperature for a certain period of time so that thermodynamic equilibrium for both pressure and temperature is achieved at the first temperature; (iii) repeating steps (i) and (ii) at an X number of temperatures until the subfreezing temperature for the biological sample is achieved, wherein X is an integer of 2 or greater. In one embodiment, X is an integer of 4 or greater. In another embodiment, X is an integer of 6 or greater. In yet another embodiment of any of the foregoing embodiments, for (ii) the sample is maintained at the temperature for a time period selected from about 1 minute to about 1 hour. In a further embodiment, for (ii) the sample is maintained at the temperature for about 30 minutes. In yet another embodiment of any of the foregoing embodiments, the subfreezing temperature of the biological sample is $-20°$ C. or lower. In a further embodiment, the subfreezing temperature of the biological sample is $-80°$ C. or lower. In still a further embodiment, the subfreezing temperature of the biological sample is $-135°$ C. or lower. In still a further embodiment, the subfreezing temperature of the biological sample is from $-135°$ C. to $-210°$ C. In another embodiment of any of the foregoing embodiments, the biological sample is one or more biomolecules, one or more cell components, one or more cells, one or more viruses, one or more embryos, one or more tissues, one or more organs or a whole organism. In a further embodiment, the one or more biomolecules is selected from amino acids, oligopeptides, polypeptides, proteins, nucleobases, nucleotides, nucleosides, oligonucleotides, polynucleotides, nucleic acids, monosaccharides, oligosaccharides, polysaccharides, carbohydrates, fatty acids, waxes, sterols, monoglycerides, diglycerides, triglycerides, phospholipids, metabolites, vitamins, hormones, steroids, or any combination of the foregoing, wherein the one of more biomolecules can be naturally occurring biomolecules, made synthetically, or a combination thereof. In yet another embodiment, the one or more cells are male or female reproductive cells. In another embodiment, the whole organism is a prokaryotic organism. In still another embodiment, the whole organism is a eukaryotic organism. In another embodiment of any of the foregoing embodiments, the biological sample further comprises one or more cryoprotectants.

The disclosure also provides a process for identifying whether a cryoprotectant or a solution thereof prevents ice crystal formation in a sample for vitrification and/or devitrification cryopreservation process, comprising placing the sample comprising the cryoprotectant or a solution thereof in an isochoric system; measuring pressure of the isochoric system while reducing the temperature of the isochoric system to a subfreezing temperature; and/or measuring pressure of the isochoric system while warming the isochoric system from the subfreezing temperature, wherein a change of pressure during the cooling or warming of the isochoric system indicates that the cryoprotectant or solution thereof fails to prevent ice formation in the sample, and wherein if there is no change of pressure in the isochoric system during cooling or heating of the isochoric system indicates that the cryoprotectant or solution has prevented ice crystal formation and is suitable for use with samples in vitrification and/or devitrification cryopreservation process.

The disclosure also provides a process for identifying whether a biological sample has or has not undergone a vitrification and/or devitrification cryopreservation process, comprising placing a biological sample in an isochoric system; measuring the pressure of the isochoric system while reducing the temperature of the isochoric system to a subfreezing temperature; and/or measuring pressure of the isochoric system while warming the isochoric system from the subfreezing temperature, wherein a change of pressure during the cooling and/or warming of the isochoric system indicates ice crystal formation and that the biological sample has not undergone a vitrification and/or devitrification cryopreservation process. In one embodiment, the biological sample comprises one or more biomolecules, one or more cell components, one or more cells, one or more viruses, one or more embryos, one or more tissues, one or more organs or a whole organism. In yet another embodiment, the one or more biomolecules is selected from amino acids, oligopeptides, polypeptides, proteins, nucleobases, nucleotides, nucleosides, oligonucleotides, polynucleotides, nucleic acids, monosaccharides, oligosaccharides, polysaccharides, carbohydrates, fatty acids, waxes, sterols, monoglycerides, diglycerides, triglycerides, phospholipids, metabolites, vitamins, hormones, steroids, or any combination of the foregoing, wherein the one of more biomolecules can be naturally occurring biomolecules, made synthetically, or a combination thereof. In another embodiment, the one or more cells are male or female reproductive cells. In yet another embodiment, the whole organism is a prokaryotic organism. In one embodiment, the whole organism is a eukaryotic organism.

The disclosure also provides a method and a device for preservation of biological materials at sub-freezing temperatures that employs a pressure transducer attached to a closed volume chamber containing the biological material to monitor and control the preservation process. In one embodiment, the chamber is a constant volume chamber.

The disclosure also provides a method and a device for preservation of biological materials in a process designed to induce preservation by vitrification (glass formation) employing a pressure transducer attached to a closed volume chamber containing the biological material to monitor and control the preservation process. In one embodiment, the chamber is a constant volume chamber.

The disclosure provides a system for preservation of biological materials at sub-freezing temperatures, comprising: a isochoric chamber; a pressure transducer that measures pressure within the isochoric chamber; a heating/cooling system in thermal communication with the isochoric chamber; a thermometer in thermal communication with internal temperature of the isochoric chamber; a computer coupled to the pressure transducer, the thermometer and the heating/cooling system that controls the rate of cooling or heating in order to maintain a constant pressure to promote vitrification. In one embodiment, the computer comprises instructions to cause the device to: cool or warm the isochoric chamber; measure a temperature via the thermometer; measure a pressure via the pressure transducer; and adjust or inhibit the cooling or warming of the isochoric chamber via the cooling system when the pressure in the isochoric chamber changes by a predetermined amount for a sample present in the chamber, wherein the change in pressure is indicative of ice crystal formation. In another or further embodiment of the foregoing, when the pressure changes the computer causes the cooling or heating to be held until a thermodynamic equilibrium is reached for both pressure and temperature. In still another embodiment of any of the foregoing, the system holds a sample at a stable pressure and temperature for isochoric vitrification. In still another embodiment of any of the foregoing, the isochoric chamber comprises rigid walls and constant volume for pressures from atmospheric pressure to 2500 bar.

DETAILED DESCRIPTION

As used herein and in the appended claims, the singular forms "a," "an," and "the" include plural referents unless the context clearly dictates otherwise. Thus, for example, reference to "a device" includes a plurality of such devices and reference to "the chamber" includes reference to one or more chambers and equivalents thereof known to those skilled in the art, and so forth.

Also, the use of "and" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although many methods and reagents are similar or equivalent to those described herein, the exemplary methods and materials are disclosed herein.

All publications mentioned herein are incorporated by reference in full for the purpose of describing and disclosing methodologies that might be used in connection with the description herein. The publications are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

Research on cryopreservation can be traced to the advances in cryogenic engineering of last century. These advances have made liquefied gases and cryogenic commercially available. In 1938, Luyet was the first to report successful cryopreservation of living biological matter in liquid nitrogen and liquid air. Luyet's cryopreservation research was focused primarily on vitrification, glass formation of water, enabled by rapid cooling of small volumes. A major breakthrough in the field of cryobiology was reported in 1949 by Polge, Smith and Parkes. They found that the addition of certain chemicals, now known as cryoprotectants, to the preservation solution, facilitates survival of living biological matter, when frozen with low cooling rates and in larger volumes. The subsequent and substantial research in the field of cryopreservation led to a fundamental understanding of the mechanisms of cell death and survival from freezing. This understanding was summarized by Mazur in a seminal, 1970 paper. The paper states that the main mechanisms affecting cryopreservation are: (i) the rate of cooling during freezing, (ii) the temperature of preservation and the time of preservation, (iii) the rate of warming during thawing, and (iv) the concentration and nature of various cryoprotectants. Today, these, are still considered the important parameters in designing cryopreservation protocols.

There are certain attributes of the cryopreservation protocols that remain, mostly, the same in all studies. First, the cryopreservation protocols are carried out under constant pressure, isobaric. In the great majority of cryopreservation studies and applications, with a few exceptions, the isobaric processes occur under atmospheric pressure. In the few exceptions, the isobaric conditions are hyperbaric. Conventional cryopreservation protocols monitor and control the temperature history during freezing, storage and sometimes thawing, and the composition of the solution. However, the volume is described only in relatively vague terms. Usually the initial volume of the thermodynamic system is specified and the type of container is described; for example, as a flexible straw, a glass capillary tube, a cryogenic vial that is either caped or uncapped. There is no information on the rigidity of the container and the changes in volume. The pressure, as mentioned earlier, is either assumed atmospheric or hyperbaric. However, the pressure in the system may change, depending on the configuration of the chamber, the materials of which the chamber is made and for example, if the chamber is sealed or not. Furthermore, there are no means for evaluating the actual volume in the system at the different stages of the cryopreservation protocols. Nevertheless, cryopreservation is a thermodynamic process that is defined by values of thermodynamic parameters such as: temperature, pressure, volume and composition. Therefore, a thermodynamic process which does not precisely specify and control the thermodynamic parameters is not repeatable and controllable. For example, two thermodynamic properties are needed to specify a one phase thermodynamic system. In a frozen system, the thermodynamic state of the frozen solution is determined by both pressure and temperature, and not just temperature. Temperature alone and a volume that is or is not constant, or a pressure that is assumed constant, does not specify the thermodynamics of a cryopreservation protocol. Thermodynamic accuracy is particularly important in attempts to develop cryopreservation protocols that employ vitrification (glass formation).

Advances in tissue engineering and the growing need for organ transplants have led to an increased interest in developing new and improved cryopreservation technologies. Currently, there is no technology for cryopreservation of large organs. While preservation of cells in small volumes may be accomplished without precise control over all the thermodynamic parameters of a cryopreservation protocol, preservation of large organs, such as a liver or a heart, require control over all the thermodynamic parameters.

The process of freezing in an atmospheric isobaric system occurs along the vertical line on the phase diagram. In contrast, the process of freezing in a constant volume system occurs along the liquidus line, to the triple point between ice I, ice III, and water. For pure water, the pressure and temperature at the triple point are −21.985° C. and 209.9 MPa, respectively. Under isobaric conditions, the entire amount of water in the system will be frozen at the triple point temperature. The extent of freezing in an isochoric system is different. Thermodynamic analysis predicts that in isochoric freezing, 45% of the water in the system will remain unfrozen at the triple point. Isochoric freezing, while maintaining a constant volume, causes an increase in pressure, to the triple point.

In a certain embodiment, the methods and devices disclosed herein utilize a concept of isochoric (constant volume) thermodynamics for cryopreservation. Provided herein are isochoric systems that have the ability to monitor and control temperature and pressure. The data presented herein clearly indicate the importance of measuring both pressure and temperature during freezing to cryogenic temperatures.

In a certain embodiment, the disclosure provides for a process for the cryopreservation of a sample, comprising: placing a biological sample in an isochoric system; reducing the temperature of the isochoric system until a subfreezing temperature is reached for the biological sample, wherein the temperature is reduced to the subfreezing temperature by a process comprising: (i) cooling the biological sample until a first temperature is reached; (ii) maintaining the sample at the first temperature for a certain period of time so that thermodynamic equilibrium for both pressure and temperature is achieved at the first temperature; (iii) repeating steps (i) and (ii) for an X number of temperatures until the subfreezing temperature for the biological sample is achieved, wherein X is an integer of 2 or greater. In further embodiment, the biological sample is reduced over 4, 5, 6, 7, 8, 9, 10, 12, 15, 20, 30 designated temperatures, or a range of temperatures including or between any two of the foregoing designated temperatures, for a certain period of time to allow for thermodynamic equilibrium for both pressure and temperature of the isochoric system. In regards to length of time for how long the sample is maintained at the designated temperature, the amount of time should be sufficient for both pressure and temperature of the isochoric system to reach thermodynamic equilibrium. In a particular embodiment, the biological sample is maintained at a designated temperature for about 1 min, about 2 min, about 5 min, about 10 min, about 20 min, about 30 min, about 40 min, about 50 min, or about 60 min, or any time range including or between any two of the foregoing designated times. It should be noted that the period of time in which a biological sample is maintained at a particular temperature is independent from all other temperatures in which the biological sample is maintained at, e.g., a sample maybe maintained at 0° C. for 30 min, at −5° C. for 5 min, at −10° C. for 10 min, etc. Alternatively, the biological sample may be maintained at each designated temperature for the same period of time, e.g., 30 minutes.

In regards to temperature, the biological sample should be cooled to a subfreezing temperature in which the biological sample is not susceptible to damage caused by unregulated chemical kinetics. While typically a subfreezing temperature of at least −80° C. is suitable for most biological samples, there are biological samples that may be cryopreserved at higher or lower subfreezing temperatures, respectively. In certain embodiments, a cryopreservation process disclosed herein call for cooling a biological sample in an isochoric system to a subfreezing temperature of about −20° C., −40° C., −60° C., −80° C., −100° C., −110° C., −120° C., −130° C., −135° C., −140° C., −150° C., −160° C., −170° C., −180° C., −190° C., −200° C., −210° C., or any temperature range including or between any two of the foregoing designated temperatures.

In regards to biological sample, any biological sample that can be cytogenetically preserved can be used in the methods disclosed herein. In a particular embodiment, the biological sample can include, but are not limited to, one or more biomolecules, one or more cell components, one or more cells, one or more viruses, one or more embryos, one or more tissues, one or more organs or a whole organism. Examples of biomolecules include, but are not limited to, amino acids, oligopeptides, polypeptides, proteins, nucleobases, nucleotides, nucleosides, oligonucleotides, polynucleotides, nucleic acids, monosaccharides, oligosaccharides, polysaccharides, carbohydrates, fatty acids, waxes, sterols, monoglycerides, diglycerides, triglycerides, phospholipids, metabolites, vitamins, hormones, steroids, or any combination of the foregoing, wherein the one of more biomolecules can be naturally occurring biomolecules, made synthetically, or a combination thereof. In a particular embodiment, the biological sample is male reproductive cells (e.g., sperm cells) or female reproductive cells (e.g., egg cells). In another embodiment, the biological sample is an embryo. In a further embodiment, the embryo is from a mammal. In yet a further embodiment, the embryo is a human embryo. In other embodiments, the biological sample is whole organism, e.g., a prokaryotic organism, or a eukaryotic organism.

In any of the methods disclosed herein, the sample (e.g., a biological sample) can comprise or further comprise one or more cryoprotectant compounds. A cryoprotectant is a substance used to protect biological tissue from freezing damage (i.e. that due to ice formation). Arctic and Antarctic insects, fish and amphibians create cryoprotectants (antifreeze compounds and antifreeze proteins) in their bodies to minimize freezing damage during cold winter periods. Cryoprotectants are also used to preserve living materials in the study of biology and to preserve food products. Cryoprotectants operate by increasing the solute concentration in cells. However, in order to be biologically viable they must easily penetrate cells and must not be toxic to cells. Some cryoprotectants function by lowering the glass transition temperature of a solution or of a material. In this way, the cryoprotectant prevents actual freezing, and the solution maintains some flexibility in a glassy phase. Many cryoprotectants also function by forming hydrogen bonds with biological molecules as water molecules are displaced. Hydrogen bonding in aqueous solutions is important for proper protein and DNA function. Thus, as the cryoprotectant replaces the water molecules, the biological material retains its native physiological structure and function, although they are no longer immersed in an aqueous environment. This preservation strategy is most often utilized in anhydrobiosis. Examples of cryoprotectants that can be used with the methods presented herein, include but are not limited to, formamide, dimethyl sulfoxide (DMSO), propylene glycol, glycerol, ethylene glycol, trehalose, sucrose, polyols, glucose, or any combination of the foregoing.

Moreover, using the methodology presented herein, the vitrification temperature of a sample can be easily identified and optimized. Vitrification, i.e. cooling to cryogenic temperatures, in such a way that water forms a glass, has become an important area of research in cryobiology. Using a solution of pure water and various concentrations of dimethyl sulfoxide (DMSO) (a commonly used cryoprotectant), the pressure and temperature history in an isochoric system was monitored to liquid nitrogen temperatures. The results suggest that the pressure measurement and the pressure transducer are a simple and very accessible device and method to identify and control optimal vitrification protocols as well as processes of devitrification.

In a particular embodiment, the disclosure provides for a process for identifying whether a cryoprotectant or a solution thereof prevents ice crystal formation in a sample for vitrification and/or devitrification cryopreservation process, comprising: placing the sample comprising the cryoprotectant or a solution thereof in an isochoric system; measuring pressure of the isochoric system while reducing the temperature of the isochoric system to a subfreezing temperature; and/or measuring pressure of the isochoric system while warming the isochoric system from the subfreezing temperature, wherein a change of pressure during the cooling or warming of the isochoric system indicates that the cryoprotectant or solution thereof fails to prevent ice formation in the sample, and wherein if there is no change of pressure in the isochoric system during cooling or heating of the isochoric system indicates that the cryoprotectant or solution has prevented ice crystal formation and is suitable for use with samples in vitrification and/or devitrification cryopreservation process.

In another embodiment, the disclosure also provides a process for identifying whether a biological sample has or has not undergone a vitrification and/or devitrification cryopreservation process, comprising: placing a biological sample in an isochoric system; measuring the pressure of the isochoric system while reducing the temperature of the isochoric system to a subfreezing temperature; and/or measuring pressure of the isochoric system while warming the isochoric system from the subfreezing temperature, wherein a change of pressure during the cooling and/or warming of the isochoric system indicates ice crystal formation and that the biological sample has not undergone a vitrification and/or devitrification cryopreservation process.

An isochoric system as used herein, is a device or devices capable of performing an isochoric process, also called a constant-volume process, an isovolumetric process, or an isometric process. An isochoric process is a thermodynamic process during which the volume of the closed system undergoing such a process remains constant. An isochoric process is exemplified by the heating or the cooling of the contents of a sealed, inelastic container: The thermodynamic process is the addition or removal of heat; the isolation of the contents of the container establishes the closed system; and the inability of the container to deform imposes the constant-volume condition.

Figure 10:
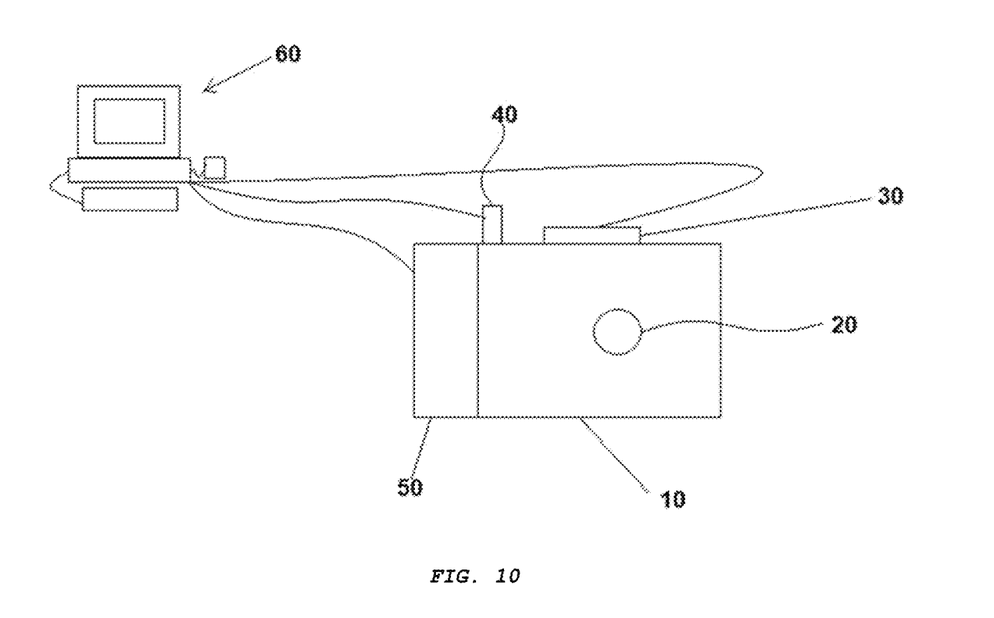
FIG. 10 is a schematic of a system of the disclosure.

FIG. 10 depicts a system of the disclosure. Depicted is an isochoric chamber 10 comprising rigid walls, typically of a material that can withstand (without deformation) pressures from atmospheric to 2500 bar. A temperature control unit (e.g., cooling, or cooling and heating) 50 is in contact with the isochoric chamber 10. Note that temperature control unit can itself be a chamber that can fit the isochoric chamber (e.g., a well, furnace, freezer etc.). Depicted is a sample 20 to be frozen. The sample, as mentioned above and elsewhere herein can be a biological sample. A pressure transducer 30 is in contact with the isochoric chamber 10 and is designed to measure changes in the pressure within the isochoric chamber 10 continuously or at desired intervals. A thermometer/temperature sensor 40 is also connected to the isochoric chamber and measures the temperature within the chamber continuously or at desired intervals. Computer 60 receives temperature and pressure information from the thermometer/temperature sensor 40 and pressure transducer 30 and, based upon the input from 30 and 40, controls the temperature control unit 50 or internal temperature of the isochoric chamber 10. For example, during operation the computer 60 causes a cooling of the isochoric chamber 10 through the temperature control unit 50. As cooling occurs, thermometer 40 and pressure transducer 30 provide temperature and pressure values to the computer 60. If, the pressure increases to a value that is indicative of ice formation (i.e., non-vitrification), then computer 60 causes the temperature control unit to stop cooling (or heating) until thermodynamic equilibrium for both pressure and temperature are achieved.

An isochoric thermodynamic process is characterized by constant volume, i.e., $\Delta V=0$. The process does no pressure-volume work, since such work is defined by $$\Delta W = P \Delta V$$

where P is pressure. The sign convention is such that positive work is performed by the system on the environment. If the process is not quasi-static, the work can perhaps be done in a volume constant thermodynamic process.

For a reversible process, the first law of thermodynamics gives the change in the system's internal energy:

$$dU = dQ - dW$$

Replacing work with a change in volume gives $$dU = dQ - PdW$$

Since the process is isochoric, $dV=0$, the previous equation now gives $$dU = dQ$$

Using the definition of specific heat capacity at constant volume, $$Cv = \frac{dU}{dT},$$

$$dQ = mc_v dT$$

Integrating both sides yields $$\Delta Q = m \int_{T_1}^{T_2} cv_d T$$

Where $c_v$ is the specific heat capacity at constant volume, $T_1$ is the initial temperature and $T_2$ is the final temperature. Concluding with:

$$\Delta Q = mc_v \Delta T$$

The following examples are intended to illustrate but not limit the disclosure. While they are typical of those that might be used, other procedures known to those skilled in the art may alternatively be used.

EXAMPLES

Isochoric System.

Figure 1A:
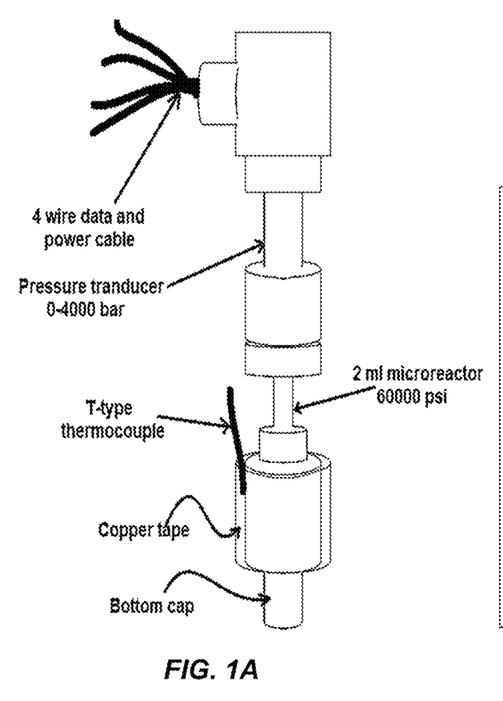
FIG. 1A-B presents an embodiment of an experimental system of the disclosure. (A) a photograph of the isochoric chamber, and (B) two isochoric devices in the cooling chamber of a Planer Kryo 10 series iii controlled rate freezer.

The isochoric freezing system is a simple constant volume chamber, capable of withstanding the pressures that develop in the system, with minimal deformation. The chamber is instrumented with a pressure transducer. The isochoric chamber is a 2 mL 316 stainless steel micro reactor MS-1 (total inner volume with fittings 3 mL, working pressure 60,000 psi) custom designed by High Pressure Equipment Company (Erie, PA, USA). Pipe sealant tape was used for sealing the device. The MS-1 micro reactor has an inside diameter of ³⁄₁₆", an outside diameter of ⁹⁄₁₆", an inside depth of 4" and an overall length of 7" (See, FIG. 1A). The isochoric micro reactor is connected to an ESI Technology Ltd HP1100 0-4000 bar (0-60,000 psi) pressure transducer, connected through an 0-5 VDC cable to a DATAQ Instruments Model DI-245 Voltage and Thermocouple DAQ 4 channel data logger connected to a laptop running DATAQ Instruments Hardware Manager. The stored data was viewed and exported from the WinDAQ Waveform browser, installed on the laptop. The pressure transducer is made up of a Silicon-on-Sapphire sensor combined with a diaphragm machined from a single piece of titanium alloy. In these experiments, to minimize inflow heat flux through the pressure transducer, polyethylene pipe insulation fixed with electrical tape was used to insulate the pressure transducer. While no pressure safety devices (i.e. rupture disk) were used on the isochoric chamber so as to minimize the thermal mass. For safety, it is recommended that the isochoric system be used with a safety head equipped with a rupture disk for a limited pressure of 400 MPa. Omega T-type Thermocouples connected to Extech Instruments EasyView™ 15 Thermometer Datalogger were also attached to the outside of the isochoric chambers as a second check to verify the set temperatures.

Figure 1B:
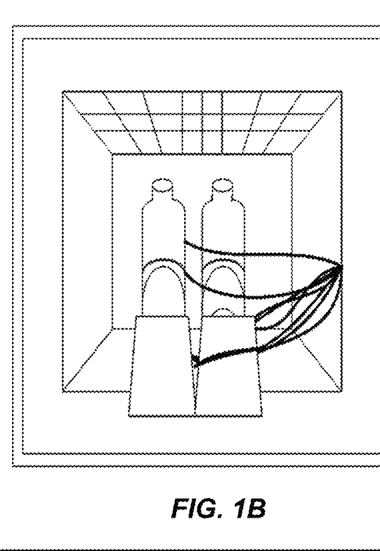

Three different experiments were performed with this setup for the isochoric chamber. In the first experiment, the isochoric system was immersed in a water-ethylene glycol bath (50/50) cooled by means of a NesLab RT-140 cooling system (Thermo Scientific, Waltham, MA, USA). This device can control temperatures to −35° C. In the second experiment, the isochoric system was placed in a Planer Kryo 10 series III controlled rate freezer, that can reach liquid nitrogen temperatures (see FIG. 1B). In the third experiment, the isochoric system was immersed in a 2 L stainless steel thermos-flask (Thermo Scientific Thermoflask 2123) of liquid nitrogen at −196° C. to achieve higher cooling rates.

Materials.

Steam distilled water (Alhambra) was used for the first and second experiments presented herein. For the third experiment, several solutions of steam distilled water (Alhambra) and dimethyl sulfoxide (DMSO with MW:78.13 g/mole, from Thermo Scientific, Prod. #20688) was used. The concentration of DMSO is expressed in w/v (g/mL). Each solution was prepared by weighing the desired DMSO mass in a 50 mL volumetric flask and then adding the volume of water to get the desired concentration and mixing. Heat is released when combining the two liquids so the volumetric flask containing the mixed solution is cooled in a cool water bath for a few seconds. More water is usually added to the mixing flask to get the desired volume because the volume typically shrinks when mixed.

Experimental Protocol.

For the first experiment, two identical micro-reactors were filled with pure distilled water (3 mL) and closed. It is important to emphasize that care must be exercised to eliminate air from the system. The two isochoric systems were then immersed in the cooling bath (NesLab) at 0° C. The temperature of the cooling bath was then set at −5° C. for 30 minutes after which it was decreased by −5° C. and held at −10° C. for another 30 minutes. The temperatures were decreased in −5° C. decrements down to −30° C. and held at each set temperature for 30 minutes. After 30 mins at −30° C., the temperatures were increased in 5° C. increments to 0° C. and held at each set temperature for 30 minutes. The pressure in the isochoric system was measured throughout the experiment. This experiment was run three times.

For the second experiment, two identical micro-reactors were filled with pure distilled water (3 mL) and closed. It is important to emphasize that care must be exercised to eliminate air from the system. The two isochoric systems were then placed in the controlled rate freezer (Planer). The freezer was used to cool and heat the chambers following a pre-programmed temperature profile. The chambers were cooled from 20° C. to −40° C. at a rate of −20° C./min and held at −40° C. for 30 minutes. Next, the chambers were cooled in −40° C. decrements down to −160° C. at a rate of −20° C./min and held at each temperature for 30 mins. After which the chambers were cooled from −160° C. to −180° C. at a rate of −20° C./min and held at −180° C. for 30 minutes. After 30 mins at −180° C., the chambers were warmed in reverse manner to the cooling. From −180° C. the chambers were heated to −160° C. at 20° C./min and held at −160° C. for 30 minutes. The chambers were then heated in 40° C. increments up to −40° C. at a rate of 20° C./min and held at each temperature for 30 min. From −40° C. the chambers were then warmed to −20° C. at a rate of 20° C./min at which point the program stopped. The pressures were measured throughout the experiment. This experiment was repeated three times For the third experiment, before filling the micro-reactor with a new solution, the micro-reactor and all its components are flushed with water and cleaned with paper towels. For each concentration, the solution was injected inside the reactor (3 mL) and the reactor was closed. It is important to emphasize that care must be exercised to eliminate air from the system. The isochoric system containing the solution was then immersed in the Thermoflask (Thermo Scientific) filled with liquid nitrogen for 15 minutes. Additional liquid nitrogen was added to the flask in order to maintain the required level of liquid nitrogen over the entire 15-minute period. After 15 minutes the isochoric system was removed and warmed in air for 45 minutes or the time it took for the pressure to return to the initial value, whichever was greater. The pressure was measured while the device was immersed in liquid nitrogen and while it was being warmed. This experiment was repeated for several concentrations of DMSO in pure water. For each solution, the experiment was repeated three times. The collected data were downloaded from the data logger and exported to Microsoft Excel for post-processing.

Results and Discussion.

Figure 2:
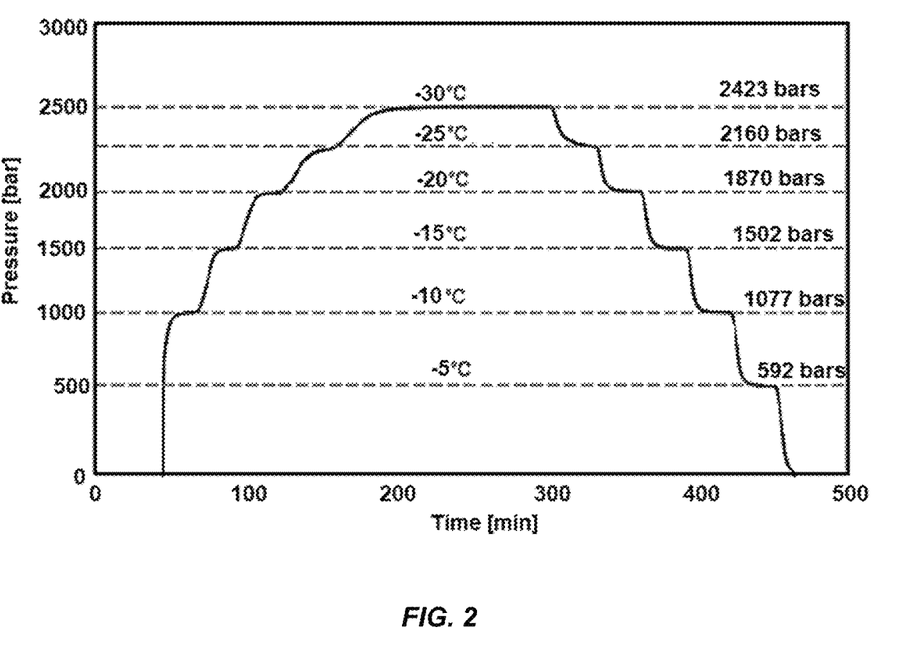
FIG. 2 provides a graph of pressure as a function of time. During certain stages of the experiment, the temperatures were kept constant, for 30 minutes. The constant temperatures are listed on the figure.

FIG. 2 shows the typical result obtained from the first set of experiments. The figure shows the pressure measured throughout the experiment, during cooling to and from −30° C. The system was maintained at preselected constant temperatures for 30 minutes, to facilitate thermodynamic equilibrium at those temperatures and pressure. The constant temperatures are listed on the figure, for the relevant pressures. Several interesting observations emerge from this figure. First, it is evident that steady state values of pressure and temperature were achieved after the 30 minutes at a certain temperature. This suggests that the measurements are for a state of thermodynamic equilibrium. The other interesting observation is that the same values of pressure and temperature were obtained during freezing and thawing, i.e. there was no hysteresis. This further bolsters the evidence for thermodynamic equilibrium. The foregoing confirms the value of measuring both temperature and pressure during cryopreservation protocols, as there are two thermodynamic measures to determine thermodynamic state. While temperature can vary in the thermodynamic system and a temperature measuring device provides data from a single site—pressure is hydrostatic and provides data throughout the system. Obviously, in a two-phase system, like for the first experiment, the thermodynamic state is determined from only one variable (temperature or pressure). However, beyond the triple point of ice I, water and ice III, both thermodynamic variables must be measured to define the thermodynamic state of the system.

Figure 3:
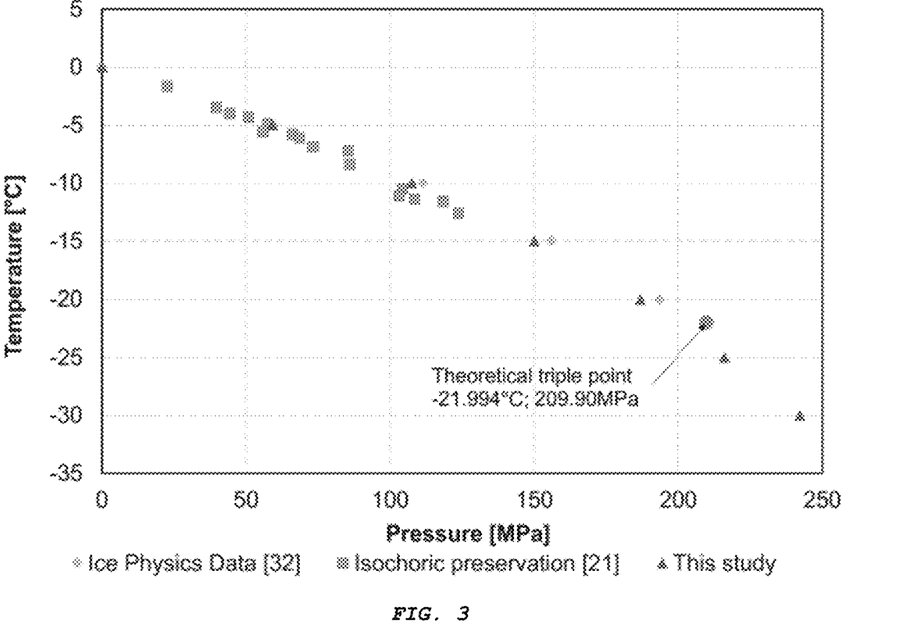
FIG. 3 provides a comparison of experimentally determined pressure and temperature using various predetermined data points.
Figure 4:
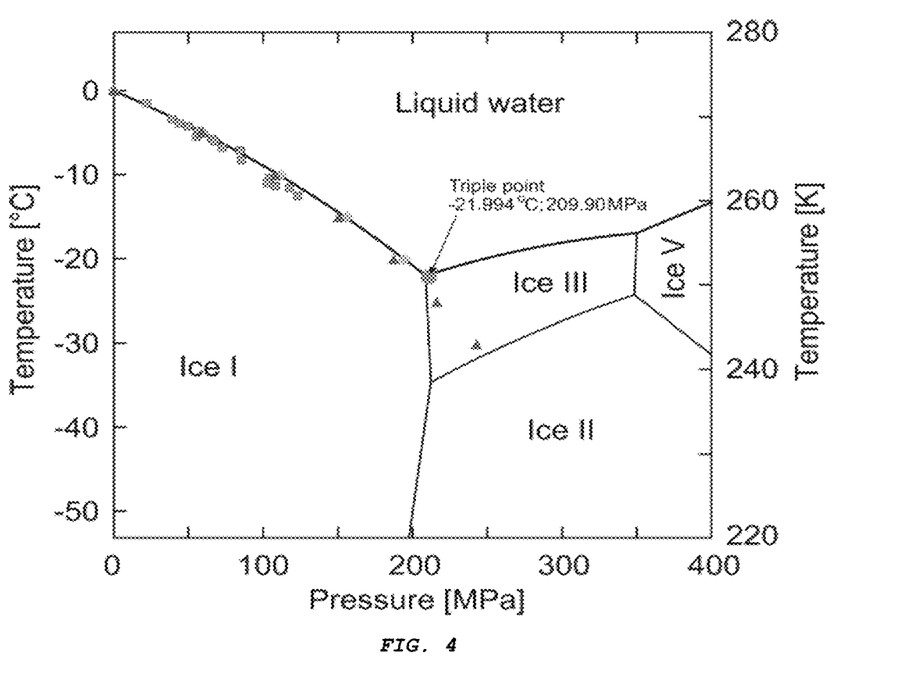
FIG. 4 presents a phase diagram where the data points from FIG. 3 are indicated.

FIG. 3 displays the pressure/temperature data, during freezing to −30° C., in comparison to the data from Preciado et al. (Cryobiology 60(1):23-29 (2016)) and Hobbs PV (Ice Physics. Oxford: Clarendon Press (1974)). The results of the experiments are in conformity with the data from those references. Unlike the references, measurements beyond the triple point were made. FIG. 3 demonstrates that the pressure increases for temperatures lower than the triple point. This was unexpected, because ice III and ice II have a higher density than ice I and therefore, the pressure would be expected to decrease. This aspect is better understood from FIG. 4, which displays the data point on the phase diagram. First of all, it is evident that all the data points to the triple point—fall on the liquidus line. However, the data points at temperatures below the triple point are at higher pressure than the triple point. Thermodynamic equilibrium would predict that as the temperature is dropped further, the temperature pressure line would follow the ice I—ice III boundary. However, it does not. A possible explanation is the formation of a metastable form of ice I—ice III mixture.

Figure 5:
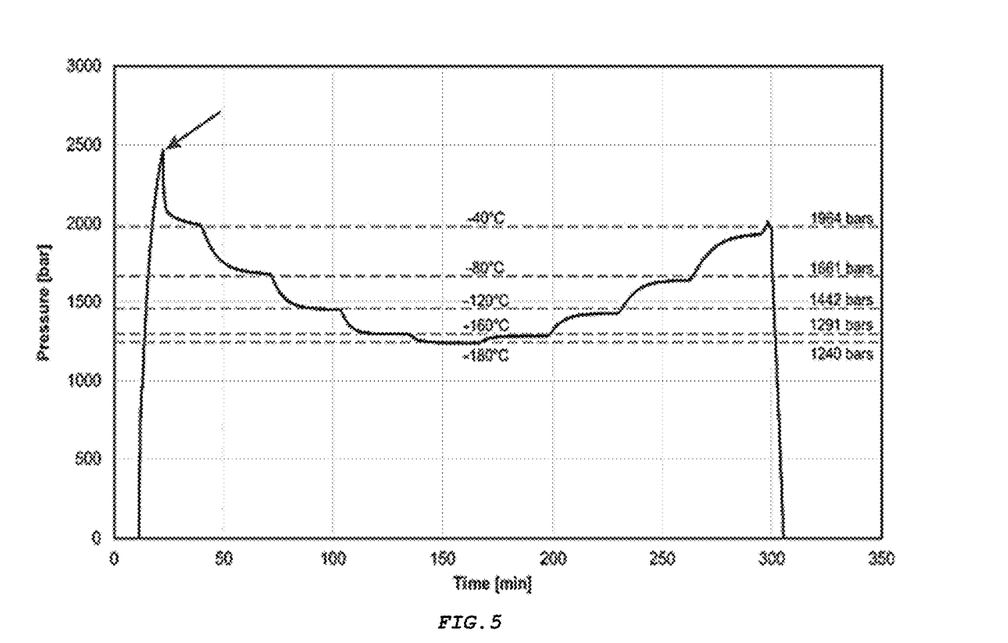
FIG. 5 provides a graph of pressure as a function of time. During certain stages of the experiment, the temperatures were kept constant for 30 minutes. The constant temperatures are listed on the figure. The arrow points to the spike in pressure during cooling to −40° C.

FIG. 5 presents the results typically seen with the second set of experiments with pure water in the temperature range from −40° C. to −180° C. Several interesting observations emerge. First as the system is cooled towards −40° C., the pressure spikes to about 250 MPa. The spike is marked in the figure with an arrow. This spike in pressure has occurred in all the experiments. The pressure spike values measured here, were similar to the values measured in the first set of experiments to −30° C. This demonstrates that the increase in pressure at temperatures lower than the triple point, is a genuine phenomenon. However, at −40° C., the pressure drops. The pressure keeps dropping at the temperatures decrease to −180° C. As the temperatures were reduced and then increased, the system was maintained at preselected constant temperatures for 30 minutes, to facilitate, thermodynamic equilibrium at those temperatures and pressure. Several interesting observations emerge from this figure. First, it is evident that steady state values of pressure and temperature were achieved after the 30 minutes at a certain temperature. This suggest that the measurements are for a state of thermodynamic equilibrium. The other interesting observation was that the same values of pressure and temperature were obtained during freezing and thawing, i.e. there was no hysteresis. This further supports the idea that the values were measured at thermodynamic equilibrium.

Figure 6:
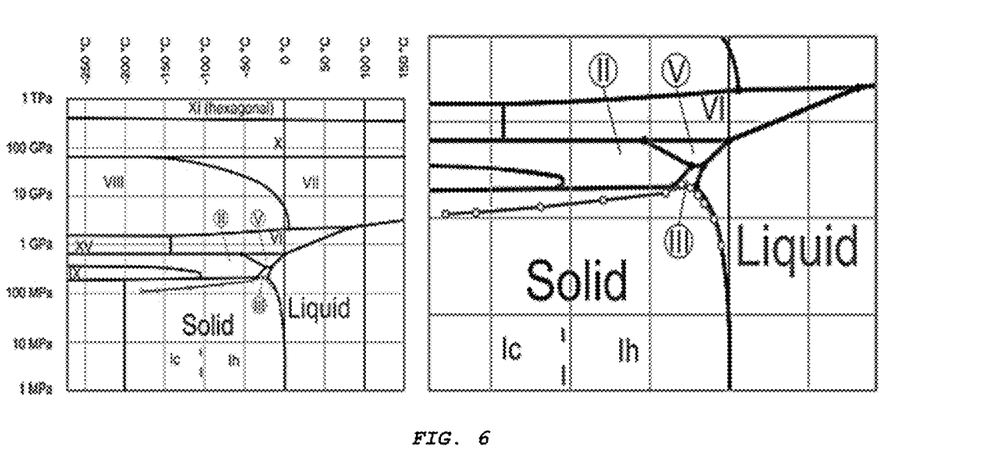
FIG. 6 presents a phase diagram where the data points from FIG. 5 are indicated.

The significance of the measurements in FIG. 5, can be better understood when plotted on a phase diagram in FIG. 6. The thermodynamic state of the system, was completely specified by the temperature and pressure (regardless of the volume). FIG. 6 shows that the ice that forms is of type I, first hexagonal and then cubic. This information could be valuable in designing optimal cryopreservation protocols and to obtain the information on the thermodynamic state of the frozen medium it is important to measure both, temperature and pressure. In a one phase system, it is impossible to determine the thermodynamic state, without measuring the values of two thermodynamic variables. The Figure also shows that the pressure decreases with a decrease in temperature. This is expected because in ice I, the density increases with a decrease in temperature to −243° C.

Figure 7:
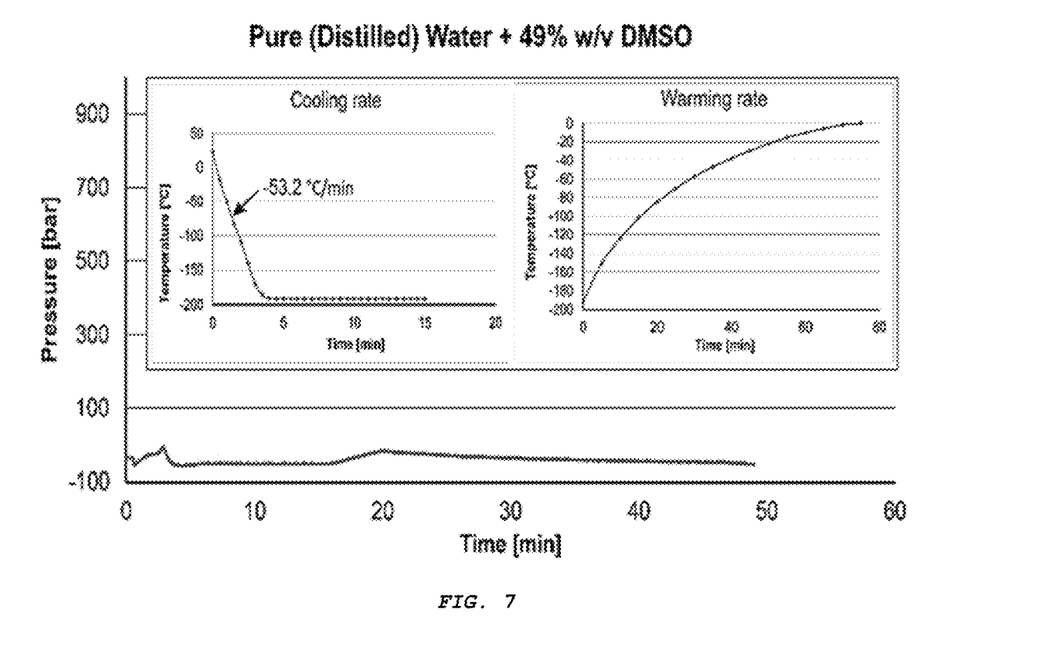
FIG. 7 presents graphs of temperature as a function of time during cooling to liquid nitrogen temperatures and from liquid nitrogen temperatures.
Figure 8:
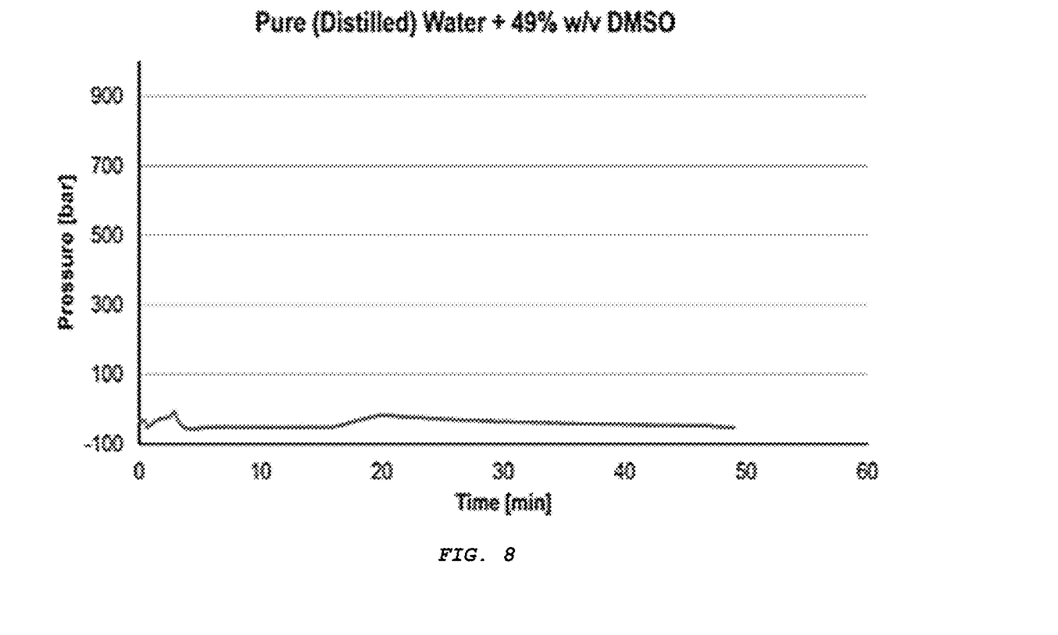
FIG. 8 provides a series of graphs of pressure as a function of time during the freezing and thawing of various solutions of water and DMSO to and from liquid nitrogen temperatures. The temperature history is given in FIG. 7.
Figure 9:
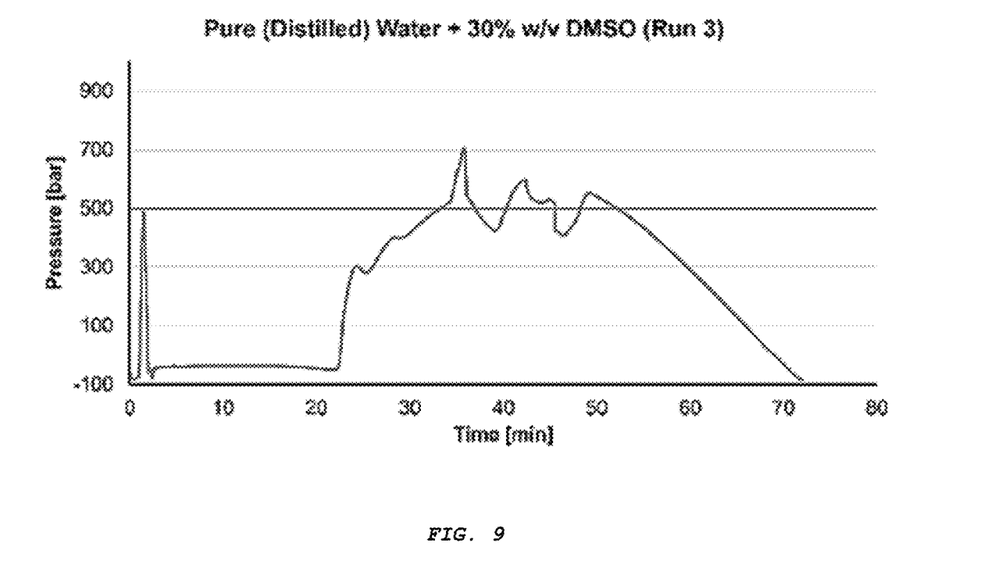
FIG. 9 provides a series of graphs of Pressure as a function of time during the freezing and thawing of various solutions of water and DMSO to and from liquid nitrogen temperatures. The temperature history is given in FIG. 7.

The geometrical configuration of the system produced the temperature history during freezing and thawing displayed in FIG. 7. No attempt was made to optimize or control the temperature history. The primary goal of this experiment was to examine the effect of various concentrations of DMSO on the measured pressure during cooling to and warming from liquid nitrogen temperatures. The results of the third set of experiments are depicted in FIGS. 8 and 9. The results in the previous figure show that the formation of ice in an isochoric system is associated with an increase in the hydrostatic pressure. In this set of experiments, the pressure as a function of time was measured in an isochoric system immersed in liquid nitrogen. FIG. 8, top left shows the pressure as a function of time in a system comprised of pure water and 49% w/v DMSO, during cooling to −180° C. and warming to ambient temperature. This composition was chosen because it produces a vitreous solution when cooled to the temperature of liquid nitrogen, i.e. no ice formation. (The temperature history is given in FIG. 7). It was postulated that when there is no ice formation in an isochoric system then there is also no increase in pressure. Indeed, the results for 49% of DMSO, demonstrate that there was no increase in pressure neither during cooling nor warming. Interestingly, the top right figure shows that there was no increase in pressure during cooling and warming for a solution of 40% w/v DMSO. This suggests that ice was not formed in this system, either. The bottom two panels in FIG. 8, were obtained for a concentration of 35% DMSO and show another interesting observation. The left-hand side figure showed a spike in pressure during freezing. This suggests that some portion of the water in the solution has frozen. However, the right hand side panel, for the same composition, showed no spike in pressure. Glass formation, vitrification, is a statistical event. The results suggest that 35% w/v DMSO and the cooling rate used in this experiment were possible at the margin of the glass formation domain, defined as the intersection between the cooling rate curve and the TTT curve. The two bottom panels in FIG. 8 demonstrated another interesting observation. The pressure increased during the warming stage of the process. The increase in pressure was related to ice formation. The bottom left hand side panel in FIG. 8 showed that there was no ice formation during cooling, but ice had formed during warming. This suggest a process of devitrification and ice crystal forming during warming. FIG. 8, illustrates the value of measuring pressure in an isochoric system. It suggests that pressure measurements could be used to identify solutions that undergo vitrification and conditions for vitrification and devitrification. This could make the research and application of vitrification for preservation of large biological samples more effective and controlled.

FIG. 9 presents the results of experiments where DMSO was used at the concentrations of 30% and 20%. The spikes in pressure during freezing in a solution of 30% DMSO and 20% DMSO, evidence that ice crystals have formed in these systems. The substantial increase in pressure during warming, also provides evidence that a process of recrystallization has occurred and that low-density ice has formed in the system.

Taken together FIGS. 2 to 9 demonstrate the value of measuring pressure during isochoric freezing in order to control and design optimal cryopreservation protocols. Pressure is a thermal variable that is easy to measure. Unlike temperature, it provides data from the entire volume, because pressure is hydrostatic. Therefore, the design and control of cryopreservation protocols, especially vitrification protocols, should control and monitor both temperature and pressure.

A number of embodiments have been described herein. Nevertheless, it will be understood that various modifications may be made without departing from the spirit and scope of this disclosure. Accordingly, other embodiments are within the scope of the following claims.

What is claimed is:

1. A system for preservation of biological materials at sub-freezing temperatures, comprising:
    an isochoric chamber;
    a pressure transducer that measures pressure within the isochoric chamber;
    a heating/cooling system in thermal communication with the isochoric chamber; and
    a computer coupled to the pressure transducer and the heating/cooling system that controls the rate of cooling or heating of the chamber in order to maintain a constant pressure to promote vitrification under thermodynamic equilibrium,
    wherein the computer comprises instructions to operate the heating/cooling system to:
    (i) cool the biological sample until a first temperature is reached, wherein the cooling is a change of about 1° C. to about 10° C. from a prior temperature;
    (ii) maintain the sample at the first temperature for a time period selected from about 10 seconds to about 1 hour so that thermodynamic equilibrium for pressure is achieved at the first temperature; and
    (iii) repeat steps (i) and (ii) at an X number of temperatures until a subfreezing temperature for the biological sample is achieved, wherein the subfreezing temperature of the biological sample is −20° C. or lower,
    wherein X is an integer of 2 or greater, and wherein the computer comprises instructions to control the heating/cooling system based only on the pressure measured via the pressure transducer.

2. The system of claim 1, wherein the computer comprises instructions to:
    cool or warm the isochoric chamber;
    measure only a pressure via the pressure transducer; and
    adjust or inhibit the cooling or warming of the isochoric chamber via the heating/cooling system when the pressure in the isochoric chamber changes by a predetermined amount for a sample present in the chamber, wherein the change in pressure is indicative of ice crystal formation.

3. The system of claim 2, wherein when the pressure changes, the computer causes the cooling or heating to be held until the thermodynamic equilibrium is reached for the pressure.

4. The system of claim 1, wherein the system holds a sample at a stable pressure for isochoric vitrification.

5. The system of claim 1, wherein the isochoric chamber comprises rigid walls and constant volume for pressures from atmospheric pressure to 2500 bar.

6. A method for preservation of biological materials in a process designed to induce preservation by vitrification (glass formation) employing a system of claim 1, comprising a pressure transducer attached to a closed volume chamber containing the biological material to monitor and control the preservation process.

7. The method of claim 6, wherein the closed volume chamber is a constant volume chamber.

8. The method of claim 7, wherein the closed volume chamber is filled with a liquid fluid.

9. The method of claim 6, wherein the one or more cells are male or female reproductive cells.

10. The method of claim 6, wherein the whole organism is a prokaryotic organism.

11. The method of claim 6, wherein the whole organism is a eukaryotic organism.

12. The method of claim 6, wherein the biological material is selected from the group consisting of one or more biomolecules, one or more cell components, one or more cells, one or more viruses, one or more embryos, one or more tissues, one or more organs or a whole organism.

13. The process of claim 6, wherein the one or more biomolecules is selected from amino acids, oligopeptides, polypeptides, proteins, nucleobases, nucleotides, nucleosides, oligonucleotides, polynucleotides, nucleic acids, monosaccharides, oligosaccharides, polysaccharides, carbohydrates, fatty acids, waxes, sterols, monoglycerides, diglycerides, triglycerides, phospholipids, metabolites, vitamins, hormones, steroids, or any combination of the foregoing, wherein the one of more biomolecules can be naturally occurring biomolecules, made synthetically, or a combination thereof.

* * * * *